United States Patent [19]

Patton

[11] Patent Number: 4,475,546
[45] Date of Patent: Oct. 9, 1984

[54] EXTERNAL FIXATION APPARATUS

[76] Inventor: Stephen M. Patton, 3823 Gold St., Omaha, Nebr. 68105

[21] Appl. No.: 507,107

[22] Filed: Jun. 23, 1983

[51] Int. Cl.³ .............................................. A61F 5/04
[52] U.S. Cl. .............................. 128/92 A; 128/92 R; 403/56; 403/90; 403/137
[58] Field of Search ................ 128/92 A, 92 R, 92 B, 128/92 E, 83; 403/90, 56, 137, 138, 143, 122

[56] References Cited

U.S. PATENT DOCUMENTS

| | | | |
|---|---|---|---|
| 2,110,414 | 3/1938 | Bell | 128/92 A |
| 2,238,870 | 4/1941 | Haynes | 128/92 A |
| 2,346,346 | 4/1944 | Anderson | 128/92 A |
| 3,240,516 | 3/1966 | Barish et al. | 403/90 |
| 3,308,812 | 3/1967 | Gidlund | 128/92 R |
| 4,127,119 | 11/1978 | Kronner | 128/92 A |
| 4,135,505 | 1/1979 | Day | 128/92 A |
| 4,273,116 | 6/1981 | Chiquet | 128/92 A |
| 4,299,212 | 11/1981 | Goudfrooy | 128/92 A |
| 4,312,336 | 1/1982 | Danieletto et al. | 128/92 A |

Primary Examiner—C. Fred Rosenbaum
Assistant Examiner—C. W. Shedd
Attorney, Agent, or Firm—Larson and Taylor

[57] ABSTRACT

An external fixation apparatus for the reduction and immobilization of the proximal end segments of a fractured bone is disclosed. The fixation apparatus includes a turnbuckle device, a ball joint device attached to the respective ends of the turnbuckle device, a locking mechanism for the ball joint devices, and a plurality of clamps which are located on tubular members extending from the ball joint devices and in which a pin embedded at one end in the fractured bone segment is received. After the pin is immovably clamped to the tubular member, the subsequent manipulation of the two tubular members relative to one another and adjustment of the turnbuckle device causes the fractured bone segments to be aligned and reduced so that the locking of the ball joint devices and turnbuckle device holds the fractured bone segments in a proper healing orientation relative to one another. Special wrenches for moving each tubular member and attached bone segment and for locking each ball joint device is provided which is supported by the associated tubular member during the reduction and immobilization of the fractured bone segments. An extension device is also provided which can be attached to one of the tubular members and which extends toward the other tubular member. A plurality of clamps are attached to this extension device so that segmented fractures or fractures close to the end of a bone can be reduced and held in place.

11 Claims, 7 Drawing Figures

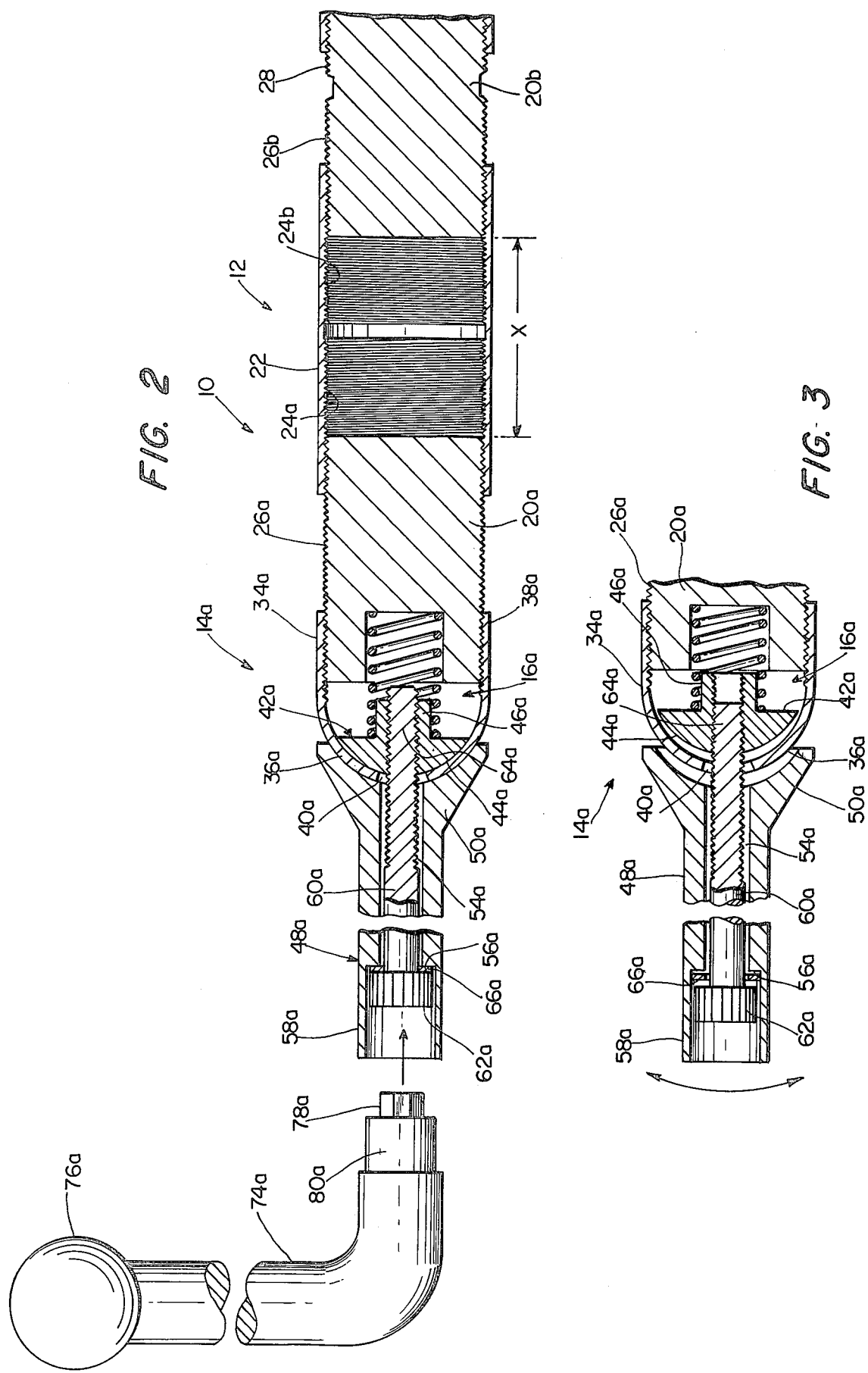

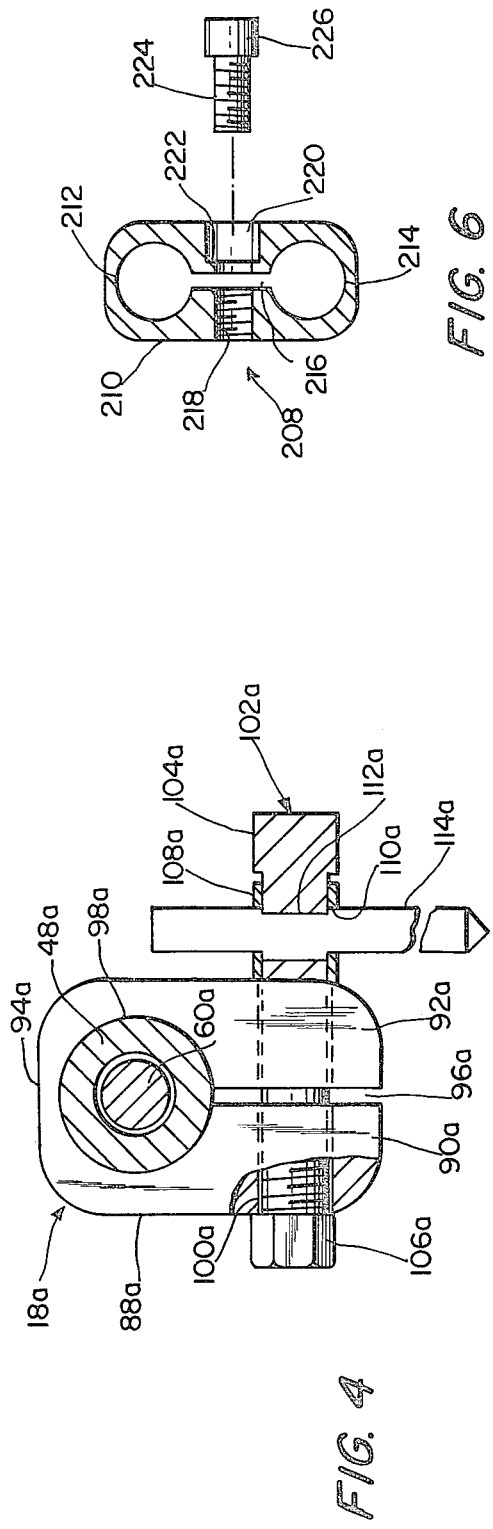
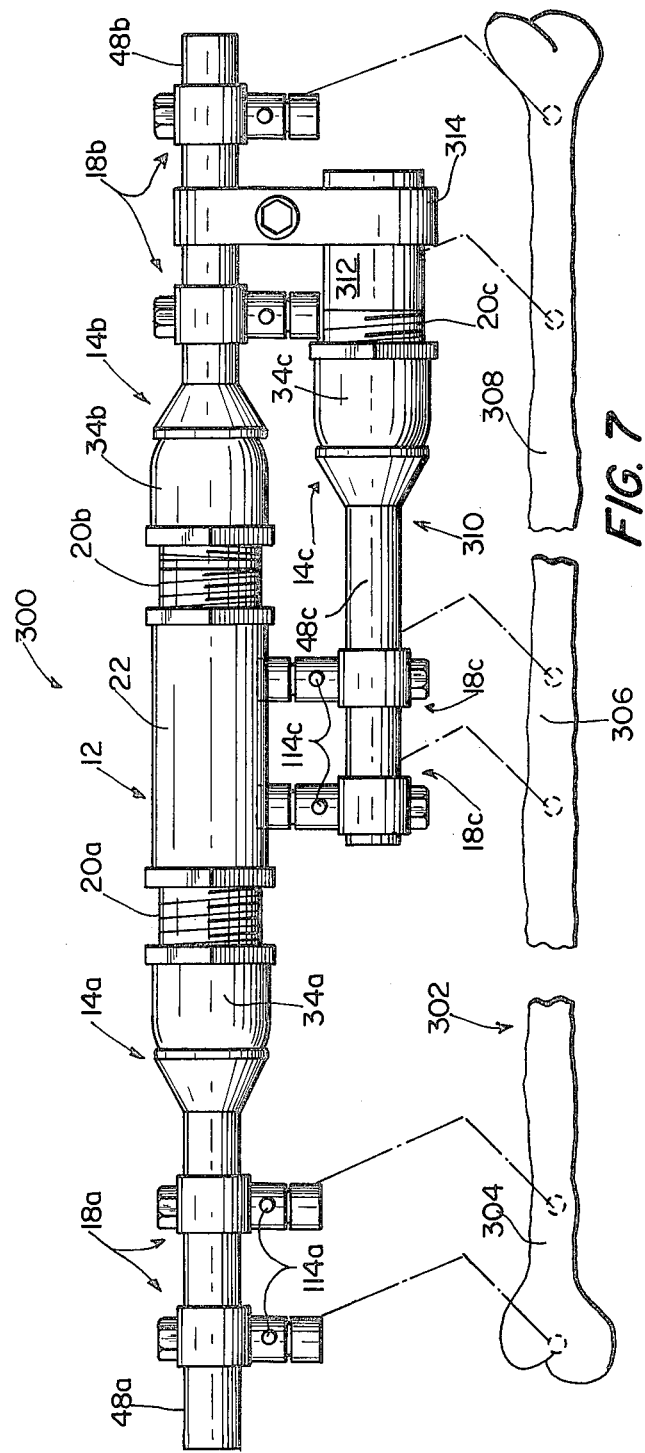

EXTERNAL FIXATION APPARATUS

FIELD OF THE INVENTION

The present invention relates generally to the reduction and immobilization of a fractured bone, and more particularly to the reduction and immobilization of the proximal end segments of a fractured bone by an externally located device.

BACKGROUND OF THE INVENTION

In the conventional treatment of broken bones, it is the usual practice to manually adjust the bone fragments, secure them in a fixed relation by the use of splints, and thereafter encase the broken limb in a plaster cast. This method requires that the limb be very carefully guarded because of the danger of disturbing the alignment of the bone fragments. In addition, the use of a plaster cast precludes treatment of any flesh wounds which may have occurred adjacent the fracture.

The treatment of a patient with an open fracture and severe soft-tissue damage presents significant problems. As discussed in "Salvage of Complicated Open Fractures by Transfixation" in the *Journal of Trama*, Vol. 16, No. 4, Pages 266 to 272 (1976) by E. B. Weis, Jr., J. B. Roberts, and P. A. Curtis, Jr., the patient with an open fracture of the shaft of the tibia with skin lost is one common example of this problem. One is reluctant to stabilize the open fracture with an implant and skin loss makes this even less attractive. Such a fracture has absolutely no inherent stability and a cast often cannot be applied with good position or alignment. When arterial injuries are present, the instability causes some concern for the graft or repair. As a result of these problems, this article proposes a method of transfixation making use of a Reduction-Retention apparatus manufactured by the Zimmer Company, Warsaw, Ind. Transfixation is a general name for methods of immobilization of fractures in long bones in which pins or screws are passed through the skin into the fragments and immobilized with extra cutaneous plaster, plastic, or metal apparatus.

The Zimmer Reduction-Retention apparatus disclosed in this article includes a central threaded compression rod on which two collars are mounted between locking nuts. The collars have extensions to which ball joint mechanisms are mounted including outwardly extending bars on which pin clamping means are provided. Set screws are provided along the proximal ends of the collars which are locked in place to hold the bars stationary. The distance between the collars is then adjusted by movement of the collars along the compression rod.

In use, the Zimmer Reduction-Retention apparatus is applied as follows. Initially, a percutaneous approach is used unless the bone is exposed by the soft-tissue injury. Thus, the apparatus is placed by making a stab incision in the skin over the location where the pin is to be placed. A trocar is then passed through this wound, impacted gently on the bone, and held in place. A drill is passed throught this trocar and through both cortices, and the pin is passed through the same trocar and screwed into the bone until the second cortex is firmly engaged. The trocar is removed and the procedure is repeated until there are two pins in each bone fragment. The pins should be reasonably well aligned with each other and with the long axis of the bone, but the pins need not be perfectly aligned. The clamp means located on the rods are then passed over respective pins with the set screws of the ball joint completely loose. The clamp means screws are then tightened. Next, the compression rods and its nuts are loosened and the handles are placed in the end of the ball joint devices. The fractured bones are then manipulated into correct alignment with these handles and the ball joint set screws tightened with the wrench. The nuts and the compression rod are then advanced to tightly lock the collars in place.

Various other external fixation devices have been disclosed in the prior art. For example, pairs of pin engaging members which are interconnected by adjustable struts having universal ball mountings to the members are disclosed in the following U.S. Pat. Nos. 2,238,869 (Haynes), 2,238,870 (Haynes), and 4,312,336 (Danieletto et al). A simple turnbuckle type mechanism for drawing two bones together by use of pins is disclosed in U.S. Pat. No. 1,997,466 (Longfellow). A turnbuckle and universal ball mounted tool used to reduce bone fragments is also disclosed in U.S. Pat. No. 2,631,585 (Siebrandt). Various outher fixation apparatus including adjustable slide mechanisms and universal mountings are disclosed in the following U.S. Pat. Nos. 4,135,505 (Day), 4,258,708 (Gentile), 4,127,119 (Kronner), 4,299,212 (Goudfrooy), and 4,273,116 (Chiquet).

Although external fixation devices have been disclosed in the prior art, the devices are often cumbersome and difficult to use. In addition, these devices require precise pin placements which may not always be possible because of the fracture site.

SUMMARY OF THE INVENTION

In accordance with the present invention, an external fixation apparatus for the reduction and immobilization of the proximal end segments of a fractured bone is provided. The external fixation apparatus includes a turnbuckle means having opposed links interconnected at their proximal ends by a central span member. Rotation of the span member adjusts the separation distance of the links. A ball joint means is attached to each respective distal end of each of the links. The ball joint means includes an elongate tubular member extending substantially coaxially away from the respective link. The ball joint means allows limited lateral movement of the distal end of the respective tubular member relative to the longitudinal axis of a respective link. A locking means is also provided for each respective ball joint means for selectively locking the ball joint means so that the respective tubular member is immovably held in position relative to a respective link. The locking means includes a locking screw extending coaxially within a respective tubular member and having a screw head located adjacent the distial end of the respective tubular member. The screw is rotated to lock the ball joint means.

A plurality of clamp means, preferably two, are located coaxially on each of the tubular members. Each clamp means is slidable along and rotatable about the respective tubular member and has a bore in which a pin embedded at one end in the fractured bone segment is received. The clamp means locates and immovably holds a respective pin at a selected position along the length of the pin and also immovably attaches the clamp means to a respective tubular member. By subsequent manipulation of the tubular members relative to one another and to the turnbuckle means, the fractured bone segments are aligned and reduced so that a subsequent locking of the locking means holds the fractured bone segments in a proper healing orientation.

According to the preferred embodiment of the present invention, each elongate tubular member includes a cylindrical socket at the distal end thereof. The screw head of the locking screw is mounted inside of this socket in abutting relationship with the tubular member. An elongate wrench having a wrench head at one end is adapted for engagement with the screw head. In addition, the wrench has a rounded shoulder portion adjacent the wrench head which fits snuggly but freely inside of the socket. In this manner, when the wrench head engages the screw head, the wrench is vertically supported by the tubular member as the shoulder engages the socket. Consequently, during reduction of the bone fragments, the wrenches can be left in place and thereafter quickly used to lock the external fixation apparatus when the bone segments are properly aligned. The ability to leave the wrench engaged with the screw during alignment and reduction also alievates the problem of fumbling with the wrench in order to insert the wrench in the screw to lock the ball joint means which can cause the bone fragments to be jarred from the aligned position.

In accordance with the preferred embodiment of the present invention, the links of the turnbuckle means include externally threaded rod portions whose threads are oppositely directed. In addition, the span member is a span tube having internal threads which mate with the external threads of the links. The ball joint means also includes a joint tube having a convexly rounded end at one end with a central aperture in the rounded end which opens into a central bore. The rounded end mates with a concave proximal portion of a respective tubular member. The joint tube has internal screw threads at the other end so that the joint tube is attached to the external threads of a respective rod portion.

In order to lock the turnbuckle means into position, two lock nuts are provided on each rod portion. One of the nuts is movable into an abutting engagement with the proximal end of a respective joint tube and the other nut is movable into an abutting engagement with the respective end of the span tube.

The locking means provided for the ball joint means includes a lock nut having a convex end which mates with the rounded end of a respective joint tube. On the other end of the lock nut is an extension. The screw passing through the aperture in the rounded end is suitably engaged in the lock nut. A compression spring which frictionally engages the lock nut extension at one end is attached at the other end to the distal end of a respective rod portion. In this manner, the lock nut is held in place adjacent the rounded end of the joint tube and is held frictionally against rotation so that locking of the ball joint means is easily achieved by rotation of the screw.

The clamp means by which the pin which is attached to a bone fragment is clamped to the tubular member includes a clamp body having a generally U-shaped cross section. The clamp body includes opposed arms having a slot therebetween and a central portion connecting the opposed arms. A central aperture is provided in the central portion and opens along the slot between the arms. The tubular member is slidably received in the central aperture so that the clamp body can both translate and rotate. A lateral aperture also extends through both opposed arms. On one end of the lateral aperture, on the outer surface of one arm, an elongate collar having a transverse aperture in which a pin is received is provided. A threaded bolt having a head and a transverse aperture in which a pin is received is also provided. The transverse aperture of the threaded bolt is located at a distance from the head of the bolt which is slightly larger than the distance of the aperture in the collar from the end of the collar. A nut located adjacent the outer surface of the other of the arms is also provided which is threadably received on the end of the bolt.

When the clamp means is assembled, the bolt is received in the lateral aperture of the clamp body with the collar around the bolt and the collar extending on one side of the opposed arm against the head of the bolt. The threaded end of the bolt is received in the nut on the other side of the opposed arms and before tightening the clamp means is slidable along and rotatable about the respective tubular member. Before the nut is tightened on the bolt, a pin is also easily located in the transverse aperture of the collar and of the bolt and the clamp means is easily rotated or slidable to accomodate the position of the pin. When the bolt and nut are tightened, the collar is pulled toward the nut to clamp the pin in the collar and bolt by a shearing force due to the different distances of the transverse apertures from the surface of the arm of the clamp body. This shearing force also pulls the opposed arms together to clamp the clamp body to the tubular member.

An extension means is also provided with the present invention which is attached to one of the tubular members and extends substantially parallel to that tubular member toward the other tubular member. A plurality of clamp means are attached to this extension means so that segmented fractures and fractures close to the end of the bone can be reduced and held in a healing orientation. In one embodiment, the extension means includes a third link, a third extension clamp means for clamping the third link at a selected position along the third link and along the one of the tubular members, a third ball joint means attached to the proximal end of the third link and including an elongate third tubular member extending substantially coaxially away from the third link and to which the plurality of clamp means are attached, and a locking means for the third ball joint means.

It is a feature of the present invention that an external fixation apparatus which is easily manipulated to bring the fractured bone segments together is provided.

It is also a feature of the present invention that the wrenches which are used to tighten the locking means for the ball joint means can be vertically supported in a position where these wrenches are immediately ready to lock the ball joint means in place.

It is a further feature of the present invention that an extension means is provided whereby segmented or comminuted fractures or fractures close to the end of a bone can be held in place.

Still another feature of the present invention is that the pins which are embedded in the fractured bone segments need not be longitudinally alighed, but instead can be oriented to provide the best gripping of the bone segments and the clamp means adjusted to receive the pins in this preferred orientation.

Other features and advantages of the present invention are stated in or apparent from a detailed description of a presently preferred embodiment of the invention found hereinbelow.

BRIEF DESCRIPTION OF THE DRAWINGS

FIG. 2 is a cross-sectional view of the external fixation apparatus depicted in FIG. 1 taken along the line 2—2 together with the locking wrench utilized with the present invention.

FIG. 3 is a cross-sectional view of the ball joint depicted in FIG. 2 in the loosened position.

FIG. 4 is a left side view in partial cross section of the pin clamping means depicted in FIG. 1.

FIG. 6 is a cross-sectional side view of the connecting clamp depicted in FIG. 5.

FIG. 7 is a top plan view of still another alternative embodiment of an external fixation apparatus according to the present invention.

DETAILED DESCRIPTION OF THE PREFERRED EMBODIMENTS

Figure 1:
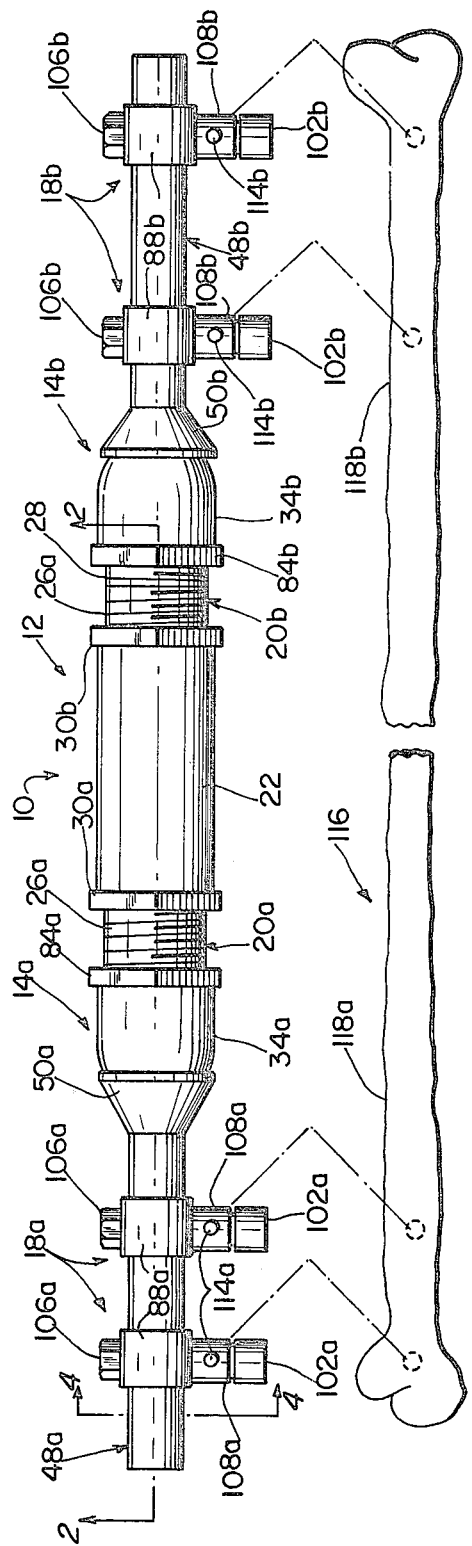
FIG. 1 is a top plan view of an external fixation apparatus according to the present invention.

With reference now to the drawings in which like numerals represent like elements throughout the several views, a presently preferred embodiment of an external fixation apparatus 10 is depicted in FIGS. 1 and 2. External fixation apparatus 10 includes a turnbuckle means 12, a ball joint means 14a and 14b on either side of turnbuckle means 12, a locking means for each ball joint means such as locking means 16a depicted in FIGS. 2 and 3, and a plurality of clamp means 18a and 18b located on respective ends of external fixation apparatus 10.

As shown in greater detail in FIG. 2, turnbuckle means 12 includes opposed elongate links 20a and 20b which are interconnected by a central span member 22. Span member 22 includes internal threaded portions 24a and 24b. Threaded portion 24a has right hand threads while threaded portion 24b has oppositely directed left hand threads. Threaded portions 24a and 24b threadably engage mating threaded portions 26a and 26b on the proximal ends of links 20a and 20b, respectively. As shown, the right hand threads of threaded portion 26a on link 20a extend along the entire length of link 20a. However, the left hand threaded portion 26b of link 20b extends only halfway along the length of link 20b, and link 20b includes a separate threaded portion 28 containing right hand threads along the remainder of the length of link 20b.

It should be appreciated that by rotation of span member 22 relative to links 20a and 20b, the separation distance "x" between links 20a and 20b is easily varied. As shown in FIG. 1, lock nuts 30a and 30b are also provided on threaded portions 26a and 26b of links 20a and 20b, respectively. By advancing lock nuts 30a and 30b toward one another and into abutting relationship with span member 22, further rotation of span member 22 can be prevented so that the separation distance "x" of links 20a and 20b is fixed. Lock nuts 30a and 30b have been omitted from FIGS. 2 and 3 for clarity.

Attached to the distal end of link 20a is ball joint means 14a which is depicted in greater detail in FIGS. 2 and 3. FIG. 2 depicts ball joint means 14a in the locked or tightened position while FIG. 3 depicts ball joint means 14a in the unlocked or loosened position. As ball joint means 14a and 14b contain identical elements, only ball joint means 14a will be described in detail and the corresponding elements of ball joint means 14b will be identified with the same numeral but with a "b" suffix.

Ball joint means 14a includes a joint tube 34a having a convexly rounded end 36a. Joint tube 34a includes an internally threaded portion 38a which is threadably received on the distal end of threaded portion 26a of link 20a. An aperture 40a is provided in the center of rounded end 36a. Located adjacent rounded end 36a and inside of joint tube 34a is a lock nut 42a having a convex end 44a which mates with the inside surface of rounded end 36a. At the other, proximal end, lock nut 42a includes an integrally formed extension collar 46a.

Located substantially coaxially with the longitudinal axis of link 20a is a tubular member 48a. Tubular member 48a includes a proximal end 50a having a concave shape which mates with rounded end 36a of joint tube 34a. Tubular member 48a includes a central bore 54a and, at the distal end of bore 54a, an abutment 56a. Extending beyond abutment 56a is a cylindrical socket 58a. Located in bore 54a of tubular member 48a is a socket head cap screw or locking screw 60a having a head 62a and a threaded end 64a which extends beyond bore 54a and is threadably received in lock nut 42a. Preferably, a thrust washer 66a made of stainless steel is located between screw head 62a and abutment 56a.

As shown in FIG. 3, when locking screw 60a is not tightened against abutment 56a, the distal end of tubular member 48a is free to move laterally relative to the longitudinal axis of tubular member 48a. The amount of movement is limited by the engagement of locking screw 60a with the walls defining aperture 40a and is preferably about 20 degrees in any direction.

When ball joint means 14a is in the loosened or unrestrained position depicted in FIG. 3, locking screw 60a is not tightened into lock nut 42a. When it is desired to lock tubular member 48a in a particular orientation relative to joint tube 34a, locking screw 60a is advanced into lock nut 42a until head 62a abuts against abutment 56a and convex surface 44a of lock nut 42a is pulled into engagement with rounded end 36a. Thus, locking screw 60a and lock nut 42a are used as locking means 16a, with locking means 16a shown in the locked position in FIG. 2.

In order to prevent lock nut 42a from rotating in joint tube 34a as locking screw 60a is rotated, one end of a helical coil spring 68a is located around extension collar 48a of lock nut 42a to frictionally grip lock nut 42a. The other end of spring 68a is frictionally retained in a recess 70a provided in the distal end of link 20a. In this manner, lock nut 42a is frictionally held against rotation as locking screw 60a is rotated in either direction. In addition, it should be noted that lock nut 42a is conveniently held in a position to receive locking screw 60a when locking screw 60a is initially inserted into lock nut 42a during assembly of external fixation apparatus 10.

Locking means 16a also includes a wrench 74a. Wrench 74a has a T-handle 76a and a wrench head 78a which is adapted to engage screw head 62a. Conveniently, wrench head 78a is a hexagonally shaped member which snugly fits in a matingly shaped recess in the center of screw head 62a.

It should also be noted that wrench 74a includes a circular shoulder portion 80a immediately adjacent wrench head 78a. Circular shoulder portion 80a is sized to fit snugly but freely within cylindrical socket 58a of tubular member 48a. When wrench head 78a is engaged with screw head 62a, wrench 74a is easily supported vertically in tubular member 48a by the engagement of circular shoulder portion 80a with cylindrical socket 58a.

With reference again to FIG. 1, it should be appreciated that locknuts 84a and 84b are provided on the distal end of threaded portion 26a of link 20a and on the threaded portion 28 of link 20b. Lock nuts 84a and 84b are snugged into abutment with the proximal ends of joint tubes 34a and 34b, respectively, to prevent any further rotation of joint tubes 34a and 34b once external fixation apparatus 10 has been assembled.

Depicted in FIG. 4 is a typical clamp means 18a which is shown attached to tubular member 48a. Clamp means 18a includes a clamp body 88a which has a generally U-shape when viewed in cross section as shown in FIG. 4. Clamp body 88a includes opposed arms 90a and 92a and a central portion 94a. Located between arms 90a and 92a is a slot 96a which opens into a central aperture 98a in central portion 94a. Tubular member 48a is slidably received in central aperture 98a. A lateral aperture 100a extends through arms 90a and 92a as shown.

Extending through lateral aperture 100a is a socket head cap screw or bolt 102a having a head 104a one one end and a nut 106a threadably received on the other end. Located about bolt 102a adjacent arm 92a is a collar 108a. Collar 108a has a transverse aperture 110a therethrough. Bolt 102a also has a transverse aperture 112a therethrough which is spaced at a distance from the innermost portion of the head 104a of bolt 102a which is slightly larger than the distance of transverse aperture 110a in collar 108a from the end of collar 108a adjacent head 104a. It should be appreciated that when nut 106a is not tightened on bolts 102a, transverse aperture 110a can be easily aligned with transverse aperture 112a so that a suitable pin 114a is passable therethrough.

Clamp means 18a depicted in FIG. 4 is shown in the clamped position. Initially, nut 196a is aligned with transverse aperture 110a in collar 108a. In this condition, bolt 102a and nut 106a exert no pinching effect on arms 90a and 92a. Consequently, pin 114a is easily insertable in transverse apertures 112a and 110a. Upon tightening of nut 106a while holding head 104a stationary, a shearing force is exerted on pin 114a by the movement of bolt 102a relative to collar 108a. This causes the deformation of pin 114a depicted and results in pin 114a being positively held relative to clamp body 88a. In addition, this shearing force causes arms 90a and 92a to be pinched toward one another and the width of slot 96a to be reduced. By properly sizing aperture 98a, the pinching action of arms 90a and 92a also securely attaches clamp body 88a to tubular member 48a. Thus, no relative movement is allowed between pin 114a and tubular member 48a when clamp means 18a is in the clamped position. It should be appreciated that in the unclamped position, before insertion of pin 114a, clamp body 88a is freely slidable along tubular member 48a and is additionally rotatable about the longitudinal axis of tubular member 48a.

A proposed use of external fixation apparatus 10 is illustrated in FIG. 1 with respect to bone 116 having bone fragments 118a and 118b. Initially, after the fracture of bone 116 is diagnosed, and it is determined that external fixation is necessary, the physician determines which locations in bone fragments 118a and 118b are appropriate for reception of suitable pins 114. Typically, self-cutting, self-threading Steinmann pins which are well known in the art, or other suitable pins, are utilized. Pins 114a and 114b are then suitably inserted into bone fragments 118a and 118b, respectively, in the locations deemed appropriate which are, for example, shown in phantom in bone 116. Pins 114a and 114b are inserted in bone 116 in the same manner as described above with respect to the operation of the Zimmer Reduction-Retention apparatus. However, it should be noted that with external fixation apparatus 10, there is no need to align pins 114a and 114b in a substantially straight line, and additionally that adjacent pins 114a or 114b need not be parallel to one another or contained in the same plane. For example, although adjacent pins 114a cannot be located on opposite sides of bone fragment 118a, adjacent pins 114a can be significantly skewed with respect to one another and still be locatable in respective clamp bodies 88a mounted on tubular member 48a. This allows pins 114a and 114b to be located in the most appropriate or strongest positions to provide the greatest holding power on respective bone fragments 118a and 118b.

Once pins 114a and 114b are implanted in bone fragments 118a and 118b, respectively, bolts 102a and 102b with associated collars 108a and 108b are located on respective pins 114a and 114b. This is accomplished for each pin 114a by aligning apertures 110a and 112a and inserting pin 114a therethrough. Pins 114b are similarly inserted in bolts 102b. Without bolts 102a and 102b, clamp bodies 88a and 88b are freely movable on respective tubular members 48a and 48b. Therefore, with tubular members 48a and 48b connected by loosened turnbuckle means 12, tubular members 48a and 48b are moved adjacent respective bolts 102a and 102b. Next, one clamp body 88a is rotated and/or translated relative to tubular member 48a to align lateral aperture 100 with a respective bolt 102a. Bolt 102a is then inserted therethrough. Clamp bodies 102b are similarly aligned relative to bolts 102b, and bolts 102b inserted therethrough.

Next, nuts 106a and 106b are then tightened on respective bolts 102a and 102b. With reference to clamps means 18a depicted in FIG. 4, it can be seen that this is easily accomplished by rotating nut 106a with a second suitable wrench relative to bolt 102a which is held stationery by another suitable wrench attached to head 104a. As discussed above, this causes pin 114a to shear and be securely held to clamp body 88a and a pinching action of arms 90a and 92a to securely attach clamp body 88a to tubular member 48a. In a similar manner, clamp means 18b is attached to pins 114b. At this time, the portions of pin 114a and 114b extending above clamp means 18a and 18b, respectively, are cut off so as not to interfere with the subsequent reduction and immobilization of bone fragments 118a and 118b.

After pins 114a and 114b are secured to tubular members 48a and 48b, respectively, the physician proceeds to extend (if necessary), align and reduce bone fragments 118a and 118b to the proper healing orientation. It should be noted that this is done with bone 116 substantially horizontal. Thus, turnbuckle means 12 is initially operated to extend bone fragments 118a and 118b as necessary. Next, wrench 74a is quickly and easily inserted in cylindrical socket 58a with wrench head 78a engaging screw head 62a. A similar wrench is also engaged in the other side in tubular member 48b. Using these wrenches for leverage, tubular members 48a and 48b are moved relative to one another to similarly move bone fragments 118a and 118b as desired. It should also be noted that ball joint means 14a and 14b are in the loosened position depicted in FIG. 3 so that tubular members 48a and 48b are not restrained against relative movement. Once bone fragments 118a and 118b have been brought into the proper alignment, wrench 74a is used to turn locking screw 60a and hence lock ball joint means 14a securely. The other wrench is similarly used to lock ball joint meand 14b in place. Thus, bone fragments 118a and 118b are quickly and easily aligned relative to one another and held in this aligned orientation.

Once bone fragments 118a and 118b are aligned, turnbuckle means 12 is used to bring these aligned fragments 118a and 118b together. This is easily accomplished by rotating span member 22. It should be noted that lock nuts 30a and 30b have been advanced toward the distal ends of links 20a and 20b, respectively, so as not to interfere with the movement of span member 22 prior to this time. After bone fragments 118a and 118b are brought into contact with one another, lock nuts 30a and 30b are moved into abutting engagement with span member 22 to securely hold span member 22 in place. At this time, bone fragments 118a and 118b are securely held in the healing orientation. If desired, the orientation of bone fragments 118a and 118b can be checked at this time.

It should be appreciated that the provision of circular shoulder portion 80a on wrench 74a which engages cylindrical socket 58a provides not only a convenient means of leverage on tubular member 48a, but also serves to retain wrench 74a attached to tubular member 48a and vertically supported thereby during alignment. Therefore, wrench 74a remains in place during this critical operation without having to be physically held there so that wrench 74a is always available for use when needed. The similar wrench in tubular member 48b is also similarly supported and always ready for use.

Figure 5:
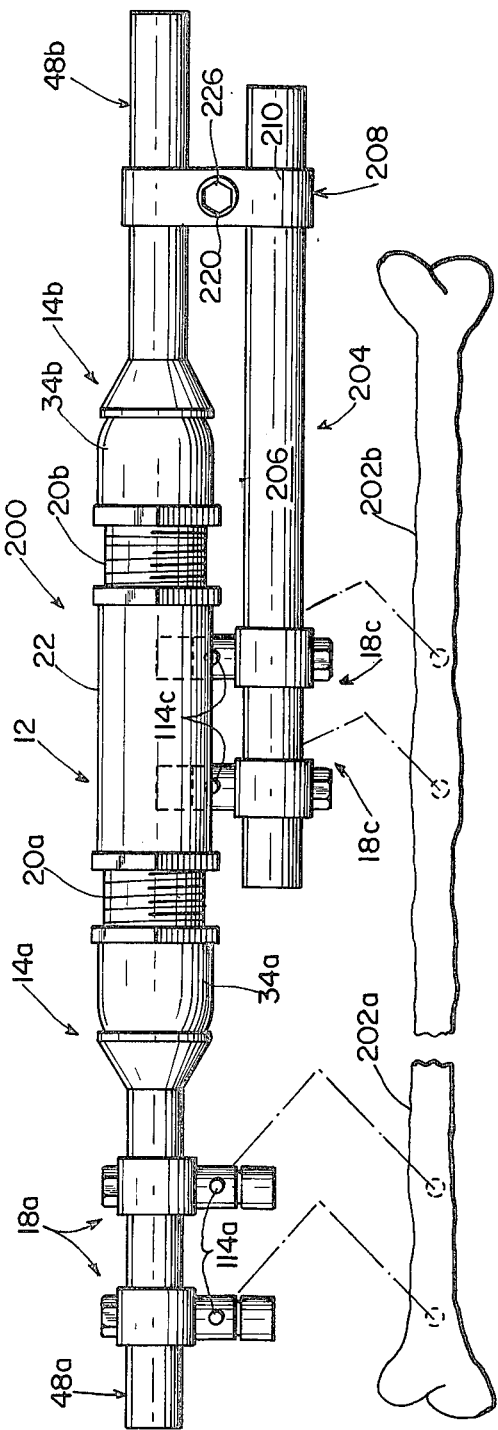
FIG. 5 is a top plan view of an alternative embodiment of an external fixation apparatus according to the present invention.

With reference now to FIG. 5, a second embodiment of an external fixation apparatus 200 is depicted. External fixation apparatus 200 is designed to reduce and immobilize bone fragments 202a and 202b where the break between bone fragments 202a and 202b is close to the end of one bone fragment such as bone fragment 202a. External fixation apparatus 200 is essentially the same as external fixation apparatus 10 with the addition of an extension means 204. For this reason, the same elements of external fixation apparatus 200 which have been described above with respect to external fixation apparatus 10 are identified using the same numerals as used above with external fixation apparatus 10.

As described above with respect external fixation apparatus 10, external fixation apparatus 200 includes a turnbuckle means 12, ball joint means 14a and 14b, a locking means for ball joint means 14a and 14b, and clamp means 18a. External fixation apparatus 200 does not include clamp means 18b, but instead has clamp means 18c. As shown, clamp means 18c are located on a rod 206 which extends parallel to the longitudinal axis of tubular member 48b. Rod 206 is immovably attached to tubular member 48b by a pinch clamp 208.

Pinch clamp 208 is depicted in greater detail in FIG. 6. Pinch clamp 208 includes a clamp body 210 in which apertures 212 and 214 are located. A slot 216 extends between apertures 212 and 214. Located on one side of slot 216 is a threaded aperture 218. On the other side of slot 216 is a coaxial aperture 220 which is larger than threaded aperture 218 and which includes a shoulder portion 222. Threadably received in threaded aperture 218 is a bolt 224 having a head 226. When bolt 224 is threadably received in threaded aperture 218 and screwed down until head 226 engages shoulder 222, further rotation of bolt 224 causes the central portion of clamp body 210 to collapse and exert a pinching effect on apertures 212 and 214. As shown best in FIG. 5, tubular member 48b and rod 206 are received in one or the other of apertures 212 and 214 so that the tightning of bolt 224 securely attaches rod 206 relative to tubular member 48b. Prior to tightening of bolt 224, it should be appreciated that both tubular member 48b and rod 206 are easily slidable in pinch clamp 208 and hence easily slidable relative to one another.

Instead of clamp means 18b located along tubular means 48b, external fixation apparatus 200 includes clamp members 18c located along rod 206. Clamp means 18c are substantially identical to clamp means 18a and 18b and are used to clamp pins 114c to rod 206. By use of pinch clamp 208 acting on rod 206, pins 114c are in turn securely attached to tubular member 48b.

In operation, external fixation apparatus 200 functions in the following exemplary manner. Once the physician determines that the fracture has occurred near the end of bone fragment 202a, the best location for pins 114a and 114c are determined and are, for example, indicated in phantom in bone fragments 202a and 202b. Pins 114a and 114c are then inserted in bone fragments 202a and 202b, respectively, in the manner described above with respect to the operation of external fixation apparatus 10. Next, the associated bolts of clamp means 18a and 18c ae located on pins 114a and 114c, respectively. With ball joint means 14a and 14b in the loosened position, tubular member 48a and rod 206 are moved adjacent respective pins 114a and 114c. Then, the bolts ae received in clamp means 18a and 18c as described above with respect to external fixation apparatus 10, and pins 114a and 114c attached to tubular member 48a and rod 206. Pinch clamp 208 is thereafter inserted on rod 206 and tubular member 48b, and pinch clamp 208 is tightened to secure rod 206 immovably to tubular member 48b. The operation of external fixation apparatus 200 from this point on is essentially the same as external fixation apparatus 10 described above.

It should be noted that span member 22 is in place as rod 206 is inserted in clamp means 18c and tubular member 48a is inserted in clamp means 18c as described above. Altenatively, span member 22 could be attached to links 20a and 20b after clamp means 18a and 18c have been secured. In either case, bone fragments 202a and 202b are then reduced to the appropriate healing position with suitable wrenches and by actuation of span member 22. Thereafter, ball joint means 14a and 14b are locked in place so that bone frgments 202a and 202b are correspondingly locked in the healing orientation desired. Suitable lock nuts are also tightened against the joint tubes 34a and 34b and against span member 22.

Depicted in FIG. 7 is an external fixation apparatus 300 which is a third embodiment of the present invention. External fixation apparatus 300 is essentially similar to external fixation apparatus 10 described above, and in a manner similar to external fixation apparatus 200 includes an extension means 310. External fixation apparatus 300 is used to reduce and immobilize a segmented or comminuted fracture such as that shown in bone 302 having fractured bone segments 304, 306, and 308.

Extension means 310 of external fixation apparatus 200 is constructed with elements which are substantially similar to the symmetrical halves of external fixation apparatus 10 on either side of span member 22, and these elements are identified with the same numerals but with a "c" suffix. Thus, extension means 310 includes a ball joint means 14c having a tubular member 48c extending therefrom. Located on tubular member 48c are clamp means 18c. Extending in the opposite direction from tubular member 48c is a joint tube 34c to which a link 20c is attached. Link 20c includes a threaded portion to which joint tube 34c is attached and a smooth rod portion 312 on which a pinch clamp 314 is attached. Pinch clamp 314 operates in the same manner as clamp 208 except that a larger aperture must be provided for rod portion 312 in the body of pinch clamp 314.

In operation, external fixation apparatus 300 functions in the following exemplary manner. Initially, after the physician has determined that a segmented fracture has occurred in bone 302, pins 114a and 114b are positioned in the appropriate locations of bone fragments 304 and 306, respectively. As with external fixation apparatus 10, the precise location of each set of pins 114a and 114b is chosen for convenience and best holding power without concern for aligning them along a longitudinal line relative to the different sets.

After the sets of pins 114a and 114b are in place, suitable bolts of clamp means 18a and 18b are respectively located thereon. Next, as with external fixation apparatus 10, loosely connected tubular members 48a and 48b are brought adjacent respective pins 114a and 114b and the bolts thereon inserted in clamp means 18a and 18b, respectively.

At the time, extension means 310 is loosely attached to tubular member 48b and located over bone fragment 308. Clamp means 18c are then moved to the best location adjacent bone fragment 308 and the transverse apertures through the respective bolts used as drill guides for pins 114c. After pins 114c are in place, the bolts of clamp means 18a, 18b, and 18c are tightened to securely attach respective bone fragments 304, 308, and 306 to tubular members 48a, 48c and 48b. At this point, ball joint means 14a, 14b, and 14c are in the loosened position and suitable wrenches such as wrench 74a are located in the ends of tubular members 48a, 48b, and 48c. Using these wrenches, bone fragments 302, 304 and 306 are aligned. Finally, using the closing of turnbuckle means 12, bone segments 304, 306, and 308 are brought into the appropriate healing orientation. When this occurs, pinch clamp 314 and turnbuckle means 12 are locked in place. Consequently, external fixation apparatus 300 operates to immobilize bone 302.

In accordance with the present invention, it is contemplated that ball joint means 14 allows approximately a 20 degree angle of movement of the associated tubular member 48. If desired, a greater or lesser movement can be allowed by appropriate design changes.

It should also be appreciated that turnbuckle means 12 can also be used to slightly tension the healing bone if desired.

Although the present invention has been described with respect to exemplary embodiments thereof, it will be understood by those of ordinary skill in the art that these and other variations and modifications can be effected within the scope and spirit of the invention.

I claim:

1. An external fixation apparatus for the reduction and immobilization of the proximal end segments of a fractured bone comprising:
   a turnbuckle means, including opposed elongate links interconnected at the proximal ends thereof by a central span member, for adjustably changing the separation distance of said links by rotation of said span member;
   a ball joint means attached to each respective distal end of each of said links, including an elongate tubular member extending substantially coaxially away from respective said links, for allowing limited lateral movement of the distal end of a respective said tubular member relative to the longitudinal axis of a respective said link;
   a locking means for each said respective ball joint means, including a locking screw extending coaxially within said respective tubular member and having a screw head located adjacent the distal end of a respective tubular member, for selectively locking said ball joint means by rotation of said screw whereby said respective tubular member is immovably held in position relative to said respective link; and
   a plurality of clamp means attached to respective said tubular members, each said clamp means being movable longitudinally relative to the respective said tubular member and being rotatable about the longitudinal axis of movement and having a bore therethrough in which a pin embedded at one end in the fractured bone segment is received, said clamp means being provided for locating and immovably holding a respective pin in said bore at a selected position along the length of the pin, and for immovably attaching said clamp means relative to the respective said tubular member whereby subsequent manipulation of said tubular members relative to one another and by said turnbuckle means causes the fractured bone segments to be reduced so that the subsequent locking of said locking means holds the fracture bone segments in a proper healing orientation relative to one another.

2. An external fixation apparatus as claimed in claim 1 wherein each said elongate tubular member includes a cylindrical socket at the distal end thereof inside of which said screw head is located in abutting relation to said tubular member, and further including for each said elongate member an elongate wrench having a wrench head at one end which is adapted for engagement with said screw head, said wrench having a circular shoulder portion adjacent said wrench head which fits snuggly but freely in said socket such that when said wrench head engages said screw head, said wrench is vertically supported by said tubular member as said shoulder engages said socket.

3. An external fixation apparatus as claimed in claim 2 wherein said links of said turnbuckle means include externally threaded rod portions whose threads are oppositely directed, and said span member is a span tube having internal threads mating with the external threads of said links.

4. An external fixation apparatus as claimed in claim 3 wherein each said ball joint means includes a joint tube having a convexly rounded end at one end with a central aperture in said rounded end which opens into a central bore in said joint tube, said rounded end mating with a concave proximal portion of a respective said tubular member, said joint tube having internal screw threads at the other end by which said joint tube is attached to the external threads of a respective rod portion.

5. An external fixation apparatus as claimed in claim 4 wherein said turnbuckle means includes two lock nuts threadably located on each said link, one of which is movable into abutting engagement with the proximal end of a respective joint tube and the other of which is movable into abutting engagement with the respective end of said span tube.

6. An external fixation apparatus as claimed in claim 4 wherein each said locking means includes a lock nut having a convex end which mates with the rounded end of a respective said joint tube and an extension on the other end, said respective screw passing through said aperture in said rounded end and threadably engaging said respective lock nut, said locking means further including a helical spring which frictionally engages said lock nut extension at one end and which is attached at the other end to the distal end of a respective said rod portion whereby said lock nut is held in place adjacent the rounded end of said joint tube and is held frictionally against rotation.

7. An external fixation apparatus as claimed in claim 6 wherein each said clamp means includes a clamp body which has a generally U-shape when viewed on end including opposed arms having a slot therebetween and a central portion connecting said opposed arms, a central aperture in said central portion which opens along said slot between said arms and in which said tubular member is slidably received, a lateral aperture extending through both opposed arms, an elongate collar located adjacent the outer surface of one of said arms coaxially with said lateral aperture and having a transverse aperture in which a pin is received, a threaded bolt having a head and a transverse aperture in which a pin is received with said transverse aperture at a distance from the head of the bolt which is slightly larger than the distance of said transverse aperture in said collar from the end of said collar, and a nut located adjacent the outer surface of the other of said arms and which is threadably received on the end of said bolt whereby said bolt is received in said lateral aperture of said clamp body with said collar around said bolt adjacent the head of said bolt and extending on one side of said opposed arms and with the threaded end of said bolt received in said nut on the other side of said opposed arms such that said clamp means is slidable along said tubular member until a pin is located in the transverse aperture of said collar and said bolt and said nut are tightened to pull said collar toward said nut to clamp the pin in said collar and bolt by a shearing force and to pull said opposed arms together to clamp said clamp body to said tubular member.

8. An external fixation apparatus as claimed in claim 2 and further including an extension means which is attached to one of said tubular members and which extends substantially parallel to said one of said tubular members toward the other of said tubular members and on which a plurality of clamp means are located whereby segmented fractures or fractures close to the end of a bone are reduced and held in a healing orientation.

9. An external fixation apparatus as claimed in claim 8 wherein said extension means includes a third link, an extension clamp means for clamping said third link at a selected position along said third link and along said one of said tubular members, a third ball joint means attached to the proximal end of said third link including an elongate third tubular member extending substantially coaxially away from said third link and to which said plurality of clamp means are attached for allowing limited lateral movement of the distal end of said third tubular member relative to the longitudinal axis of said third line, and a locking means for locking said third ball joint means immovably in a selected position.

10. An external fixation apparatus as claimed in claim 1 and further including an extension means which is attached to one of said tubular members and which extends substantially parallel to said one of said tubular members toward the other of said tubular members and on which a plurality of clamp means are located whereby segmented fractures or fractures close to the end of a bone are reduced and held in a healing orientation.

11. An external fixation apparatus as claimed in claim 10 wherein said extension means includes a third link, an extension clamp means for clamping said third link at a selected position along said third link and along said one of said tubular members, a third ball joint means attached to the proximal end of said third link including an elongage third tubular member extending substantially coaxially away from said third link and to which said plurality of clamp means are attached for allowing limited lateral movement of the distal end of said third tubular member relative to the longitudinal axis of said third link, and a locking means for locking said third ball joint means immovably in a selected position.

* * * * *